April 1, 1975 L. J. KOCH Plant Pat. 3,699
ALMOND TREE
Filed Jan. 17, 1974
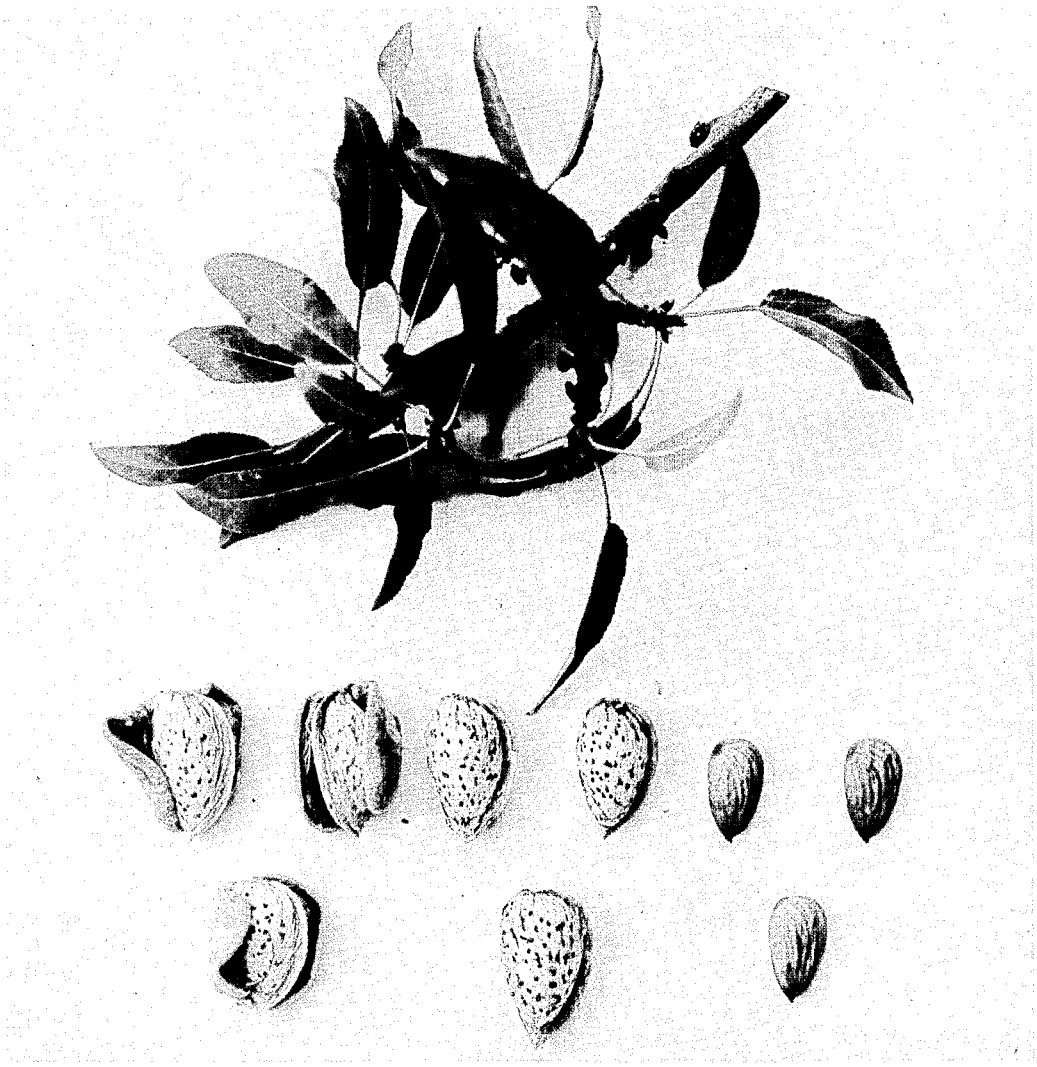

United States Patent

Plant Pat. 3,699

Patented Apr. 1, 1975

3,699

ALMOND TREE

Leroy J. Koch, 588 Bird St., Yuba City, Calif. 95991

Filed Jan. 17, 1974, Ser. No. 434,338

Int. Cl. A01h *5/03*

U.S. Cl. Plt.—30 1 Claim

ABSTRACT OF THE DISCLOSURE

An almond tree which is large, dense, vigorous, many-branched, vase-shaped, foliated with abundant medium-size, glossy green leaves, late blooming with light pink very heavy bloom resulting from fruiting buds resembling those of a peach and consistently bi-florous in the majority, and a regular and heavy to very heavy producer branched, vase-shaped, foliated with abundant medium-size, easy to hull and crack nuts borne in clusters on short spurs, and having a medium to small kernel of good quality and high flavor.

ORIGIN OF THE VARIETY

The present variety of almond tree was discovered by me growing in an orchard of Peerless (unpatened) almond trees on my ranch located near Yuba City, Sutter County, Calif.; the discovery having resulted from my recognition that the tree was late in blooming, and—upon further and continued observation—other novel characteristics, as hereinafter described, became apparent and confirmed that the tree was a new and distinct variety.

ASEXUAL REPRODUCTION OF THE VARIETY

Subsequent to my discovery of the original tree of the present variety, and upon a realization that its novel characteristics were desirable for commercial growing, I asexually reproduced the variety—first by grafting and budding on seedlings, on my behalf, by a nurseryman, and subsequently top-working by me on young Mission (unpatented) trees; such grafting and budding, and top-working, having been accomplished on my ranch located as aforesaid. Such reproductions—observed in maturity in comparison to the original tree of the variety—ran true in all respects.

SUMMARY OF THE VARIETY

The present variety of almond tree is, characteristically, large, dense, vigorous, many-branched, vase-shaped, foliated with abundant, medium-size, glossy green leaves, late blooming with light pink very heavy bloom resulting from fruiting buds resembling those of a peach and consistently bi-florous in the majority, and a regular and heavy to very heavy producer of rapidly maturing, early and easy harvesting, medium-size, easy to hull and crack nuts borne in clusters on short spurs, and having a medium to small kernel of good quality and high flavor.

The present variety of almond tree is more particularly characterized—in comparison to certain known varieties—as follows:

The vase-shaped tree, with its many branches and spurs, shows a definite "twist" as does the IXL (unpatented) when budded on bitter almond rootstock.

The foliage is of a somewhat darker, glossy green uncommon to known almond varieties, and is more dense than usual.

The fruiting buds on the tree resemble those of a peach in shape in that, prior to opening, they are round rather than the ovate shape commonly seen in almond varieties. Approximately sixty to eighty percent of the fruiting buds are bi-florous; i.e., as each bud matures it splits into two separate buds individually producing a fruiting blossom.

This is not uncommon in some varieties of peaches and is only noted occasionally in almond varieties, and then to a much lesser degree. No existing variety of almond tree, known to applicant, consistently has such a high percentage of bi-florous fruiting buds as does the present variety.

Additionally, and here again like certain peach varieties, the extreme end of the pistil emerges two or three days prior to the blossom opening. The blossom, which blooms late, is small as compared to other almond varieties, usually being about one inch in diameter and more like a peach in over-all dimensions. The petals, of the blossoms, are smooth and narrower than common to almond varieties, and instead have more resemblance to those of peach blossoms.

After the late blooming period, the fertilized nuts mature very rapidly and their size is shortly equal to the nuts of earlier blooming varieties of almonds. Further, and unlike most late-blooming almond varieties, the nuts of the present variety reach maturity early in the harvest season—again a characteristic common with peach varieties.

The nuts of the present variety closely resemble those of the Ne Plus Ultra (unpatented) in shape and texture, except that they are softer and easier to crack; while the kernels are quite similar to those of the Nonpareil (unpatented).

From the foregoing, it will be understood that the present variety of almond tree is not only novel and distinct in comparison to known almond varieties, but also has certain characteristics more common in peach varieties.

BRIEF DESCRIPTION OF THE DRAWING

The drawing is an illustration, as of harvest time and by photographic reproduction in color, of a twig with leaves, nuts in hull, nuts out of hull, and separate kernels.

DESCRIPTION OF THE VARIETY

The botanical details of this new and distinct variety of almond tree—with color definitions (except those in common color terms) referenced to Maerz and Paul Dictionary of Color—are as follows:

Tree:
- *Density.*—Dense.
- *Size.*—Large.
- *Vigor.*—Vigorous.
- *Form.*—Vase-shaped.

Trunk:
- *Form.*—Stocky.
- *Texture.*—Medium.

Branches:
- *Form.*—Stocky.
- *Texture.*—New wood—smooth. Mature wood—medium.
- *Lenticels.*—Numerous on mature wood. Large to medium size.
- *Branching habit.*—Many-branched, spreading.
- *Color.*—New wood—Red and green, glossy. Mature wood—Brown, dull.

Foliage:
- *Quantity.*—Abundant.

Leaves:
- *Size.*—Medium. Average length—2½" to 3⅛" on mature wood. Average width—¾" to 1" on mature wood. Leaves tend to be slightly larger on young vigorous shoots.
- *Shape.*—Acuminate to lanceolate. Acutely pointed.
- *Thickness.*—Medium.
- *Texture.*—Smooth.

*Margin.*—Crenate to finely serrate.

*Petiole.*—Length—Medium—average ¾" to 1". Relative length about ⅓ that of leaf. Thickness—Medium. Form—Slender.

*Glands.*—Average number—6. Alternate, medium size, reniform. Red-green-light brown. Positioned on petiole about ⅜" to ½" from base of leaf. Stipules—none.

*Color.*—Top side—Glossy green (22-L-7). Under side—Dull, lighter green (22-I-6).

Fruiting buds:

*Type.*—Approximately 60% to 80% bi-florous.

*Form.*—Nearly round-shape prior to opening, but—with maturity—split into two separate buds each producing a fruiting blossom.

Bloom:

*Amount of bloom.*—Very heavy.

*Color.*—Light pink.

*Blooming period.*—End of February to mid-March. Late—achieves full bloom with, or 3 to 5 days after, Texas (unpatented)

Crop:

*Bearing.*—Regular bearer.

*Productivity.*—Tends to alternate between very heavy and heavy.

*Distribution of nuts on tree.*—In clusters on short spurs.

*Harvest period.*—Early, usually about August 1st to August 15th, with Nonpareil or Peerless.

*Tenacity.*—Hangs well on tree. Easy to harvest. Easy to hull.

Hull:

*Outer surface.*—Smooth.

*Pits.*—None.

*Form.*—Regular.

*Thickness.*—Thick.

*Flesh.*—Fleshy.

*Suture.*—Ridged.

*Color.*—Light green with a silvery sheen.

*Dehiscence.*—Opens very freely.

*Splitting.*—Along suture—partially down back.

Nut:

*Size.*—Medium. Average length—1 3/16" to 1½" (1⅛"–1⅝" range). Average width—¾" to ⅞" (11/16"–1" range). Average thickness—9/16" to ⅝" (½"–11/16" range). Average weight—222 per pound (range 260 to 185 per pound). Above recited averages are for normal and light crops, respectively.

*Form.*—*Length/width*—Ovate. Ratio: 1.5:1. *Width/thickness*—Plump. Ratio: 1.36:1.

*Shell.*—Soft, medium thickness, smooth. *Outer shell*—Bony crumbling, a few partially adhering to hull. *Inner shell*—Thin—hard, fairly well sealed.

*Color.*—Medium light straw (11-D-3).

*Pits.*—Large, numerous, deep, irregular.

*Base.*—Dorsally oblique.

*Stem scar.*—Small, obtuse.

*Apex.*—Acute, acuminate.

*Wing.*—Broad, thin, tapered toward base.

*Inner surface.*—Medium straw color.

*Ventral streak.*—Light color, narrow, long, point obtuse.

*Percentage of kernel to nut on average sample.*—About 55% by weight.

Kernel:

*Size.*—Small to medium, depending on crop productivity. Average length—⅞" to 1" (⅞" to 1⅛" range). Average width—½" to ⅝" (½" to ⅝" range). Average thickness—9/32" (¼" to 5/16" range). Average weight—25 per ounce (29 to 21 per ounce range).

*Form.*—*Length/width*—Elongated, ovate. Ratio: 1.6:1. *Width/thickness*—Plump, flat. Ratio: 2:1.

*Base.*—Square.

*Stem scar.*—Small, obtuse.

*Apex.*—Acute, sharp, tip recurved slightly.

*Texture.*—Furrowed.

*Pellicle.*—Thin.

*Pubescence.*—Smooth.

*Color.*—Medium light brown (14-J-10) to reddish brown.

*Number of doubles.*—Very few.

*Defective kernels.*—Very few gummy or deformed kernels.

*Flavor.*—Dry, sweet, normal, but highly flavored.

*Quality.*—Good.

Susceptibility or resistance to insects and diseases: Tree is very vigorous, healthy appearing, and no unusual susceptibilities noted.

The almond tree and its nuts herein described may vary in slight detail due to climatic and soil conditions under which the variety may be grown; the present description being of the variety as grown in the Sacramento Valley of California.

I claim:

1. A new and distinct variety of almond tree, substantially as illustrated and described.

References Cited

UNITED STATES PATENTS

P.P. 3,005 11/1970 Fritz ---------- Plants—30

ROBERT E. BAGWILL, Examiner